United States Patent [19]

Hübsch et al.

[11] Patent Number: 5,034,399
[45] Date of Patent: Jul. 23, 1991

[54] SUBSTITUTED 1,8-NAPHTHYRIDINES AND THEIR USE IN MEDICAMENTS

[75] Inventors: Walter Hübsch; Rolf Angerbauer; Peter Fey, all of Wuppertal; Thomas Philipps, Cologne; Hilmar Bischoff, Wuppertal; Dieter Petzinna, Duesseldorf; Delf Schmidt, Wuppertal, all of Fed. Rep. of Germany

[73] Assignee: Bayer Aktiengesellschaft, Leverkusen, Fed. Rep. of Germany

[21] Appl. No.: 496,757

[22] Filed: Mar. 21, 1990

[30] Foreign Application Priority Data

Apr. 6, 1989 [DE] Fed. Rep. of Germany ....... 3911064

[51] Int. Cl.$^5$ .................. A61K 31/435; C07D 471/04
[52] U.S. Cl. .................... 514/300; 514/256; 544/333; 546/122
[58] Field of Search ............... 546/122; 544/333; 514/256, 300

[56] References Cited

U.S. PATENT DOCUMENTS 4,613,610  9/1986  Wareing ........................... 514/406
4,761,419  8/1988  Piccard et al. ..................... 544/333

FOREIGN PATENT DOCUMENTS 0022478   1/1981  European Pat. Off. .
0114027   7/1984  European Pat. Off. .
02322350  11/1973 Fed. Rep. of Germany .
3825611   2/1990  Fed. Rep. of Germany .

Primary Examiner—Bernard Dentz
Attorney, Agent, or Firm—Sprung Horn Kramer & Woods

[57] ABSTRACT

Inhibitors of 3-hydroxy-3-methyl-glutarylcoenzyme A reductase which are 1,8-naphthyridines of the formula in which A represents a 3- to 7-membered heterocycle which is optionally substituted, or aryl which is optionally substituted, B represents cycloalkyl or alkyl which is optionally substituted, aryl which is optionally substituted, D and E are identical or different and represents hydrogen, halogen, mercapto, hydroxyl, alkoxy, alkyl which is optionally substituted, or a group of the formula —NR$^1$R$^2$, aryl, aryloxy or arylthio having 6 to 10 carbon atoms, which is optionally substituted, Y represents a group of the formula $$-\underset{J}{\overset{}{C}}=N- \quad \text{or} \quad -\underset{Z}{\overset{}{\underset{\|}{C}}}-\underset{G}{\overset{}{N}}-$$

in which

J denotes hydrogen, hydroxyl, mercapto or halogen, or alkyl, alkoxy or alkylthio which are optionally substituted, aryloxy, benzyloxy or arylthio or a group of the formual —NR$^1$R$^2$, Z denotes oxygen or sulphur, G denotes hydrogen, alkyl or alkenyl which is optionally substituted, X represents a groups of the formula —CH$_2$CH$_2$— or —CH=CH—, and R represents a group of the formula $$-\underset{OH}{\overset{}{CH}}-CH_2-\underset{OH}{\overset{R^5}{\underset{|}{C}}}-CH_2-COOR^6 \quad \text{or} \quad$$

in which

R$^5$ denotes hydrogen or alkyl, and
R$^6$ denotes hydrogen or alkyl, which may be substituted by phenyl, or
denotes aryl or a cation, and their salts.

9 Claims, No Drawings

SUBSTITUTED 1,8-NAPHTHYRIDINES AND THEIR USE IN MEDICAMENTS

The invention relates to new substituted 1,8-naphthyridines, to intermediates for their preparation, and to their preparation and their use in medicaments.

It is known that lactone derivatives isolated from fungal cultures are inhibitors of 3-hydroxy-3-methylglutaryl-coenzyme A reductase (HMG-CoA reductase) mevinolin, EP-A 22,478; U.S Pat. No. 4,231,938]. Moreover, certain indole derivatives or pyrazole derivatives are inhibitors of HMG-CoA reductase [EP-A 1,114,027; U.S Pat. No. 4,613,610].

New substituted 1,8-naphthyridines of the general formula (I)

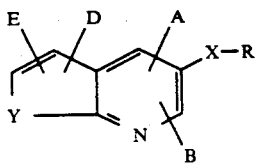

in which

A
represents a 3- to 7-membered heterocycle which may contain up to 4 sulphur, oxygen or nitrogen heteroatoms and which is optionally monosubstituted to trisubstituted by identical or different substituents from the series comprising halogen, trifluoromethyl, trifluoromethoxy, straight-chain or branched alkyl, alkoxy or alkoxycarbonyl in each case having up to 8 carbon atoms or by aryl having 6 to 10 carbon atoms, or A
represents aryl having 6 to 10 carbon atoms which is optionally monosubstituted to pentasubstituted by identical or different substituents from the series comprising straight-chain or branched alkyl, alkylthio, alkylsulphonyl, alkoxy or alkoxycarbonyl in each case having up to 10 carbon atoms, which may in turn be substituted by hydroxyl, alkoxy having up to 6 carbon atoms, phenyl or by a group of the formula -NR$^1$R$^2$, in which
R$^1$ and R$^2$ are identical or different and
denote hydrogen, aryl or arylsulphonyl having 6 to 10 carbon atoms, straight-chain or branched alkyl or alkylsulphonyl having up to 8 carbon atoms, where the last mentioned radicals are optionally substituted by aryl having 6 to 10 carbon atoms,
or denote a group of the formula -COR$^3$ in which
R$^3$
denotes straight-chain or branched alkyl or alkoxy having up to 8 carbon atoms, or phenyl,
or the aryl is substituted by aryl, aryloxy, arylthio or arylsulphonyl having 6 to 10 carbon atoms, or by halogen, nitro, cyano, trifluoromethyl, trifluoromethoxy, trifluoromethylthio, benzyloxy or a group of the formula -NR$^1$R$^2$,
in which
R$^1$ and R$^2$ have the abovementioned meaning, B
represents cycloalkyl having 3 to 8 carbon atoms, straight-chain or branched alkyl having up to 12 carbon atoms, which is optionally substituted by halogen, trifluoromethyl or alkylthio having up to 8 carbon atoms,
represents aryl having 6 to 10 carbon atoms, which is optionally substituted by halogen, cyano, nitro, trifluoromethyl, straight-chain or branched alkyl, alkoxy or alkoxycarbonyl in each case having up to 8 carbon atoms, or amino, D and E are identical or different and
represent hydrogen, halogen, mercapto, hydroxyl, alkoxy having up to 8 carbon atoms, straight-chain or branched alkyl having up to 10 carbon atoms, which is optionally substituted by hydroxyl, phenoxy, halogen, trifluoromethyl or alkylthio having up to 8 carbon atoms, or represent a group of the formula -NR$^1$R$^2$,
in which
R$^1$ and R$^2$ have the abovementioned meaning, or D and E each independently
represent aryl, aryloxy or arylthio having 6 to 10 carbon atoms, which is optionally substituted by halogen, cyano, nitro, trifluoromethyl, straight-chain or branched alkyl, alkoxy or alkoxycarbonyl in each case having up to 8 carbon atoms, or amino, Y
represents a group of the formula

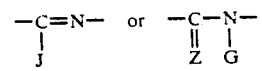

in which
J
denotes hydrogen, hydroxyl, mercapto or halogen, or denotes straight-chain or branched alkyl, alkoxy or alkylthio having up to 10 carbon atoms, which are optionally substituted by phenyl, or denotes aryloxy, benzyloxy or arylthio having 6 to 10 carbon atoms or a group of the formula -NR$^1$R$^2$,
in which
R$^1$ and R$^2$ have the abovementioned meaning,
Z
denotes oxygen or sulphur,
G
denotes hydrogen, straight-chain or branched alkyl or alkenyl in each case having up to 10 carbon atoms, which is optionally substituted by halogen, cyano, alkoxy having up to 8 carbon atoms, benzyloxy, aryl or aryloxy having 6 to 10 carbon atoms, by a 5- to 7-membered heterocycle having up to 4 nitrogen, oxygen or sulpur heteroatoms or by a group of the formula -NR$^1$R$^2$, -COR$^3$ or -COOR$^4$,
in which
R$^1$, R$^2$ and R$^3$ have the abovementioned meaning,
R$^4$
denotes hydrogen or straight-chain or branched alkyl having up to 10 carbon atoms, which is optionally substituted by hydroxyl, phenyl, halogen or cyano,
or R$^4$ denotes aryl having 6 to 10 carbon atoms, which may in turn be substituted by halogen, amino, hydroxyl, nitro or cyano, X
represents a group of the formula -CH$_2$-CH$_2$- or -CH=CH-, and
R
represents a group of the formula

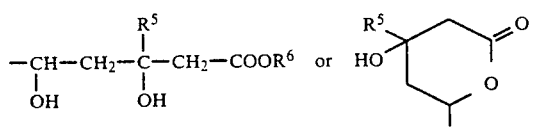

in which
R⁵
denotes hydrogen or straight-chain or branched alkyl having up to 20 carbon atoms
and
R⁶
denotes hydrogen or straight-chain or branched alkyl having up to 10 carbon atoms, which may be substituted by phenyl, or
denotes aryl having 6 to 10 carbon atoms or a cation,
and their salts have now been found.

If R⁶ forms an ester radical with the carboxyl group, then a physiologically tolerable ester radical, which is easily hydrolyzed in vivo to give a free carboxyl group and a corresponding physiologically tolerable alcohol, is preferably meant by this. These include, for example, alkyl esters (C₁ to C₆) and aralkyl esters (C₇ to C₁₀), preferably (C₁-C₄)-alkyl esters and benzyl esters. Moreover, the following ester radicals may be mentioned: methyl esters, ethyl esters, propyl esters and benzyl esters.

If R⁶ represents a cation, then a physiologically tolerable metal cation or ammonium cation is preferably meant. Preferred cations in this connection are alkali metal or alkaline earth metal cations such as, for example, sodium, potassium, magnesium or calcium cations, and also aluminum or ammonium cations, and non-toxic substituted ammonium cations of amines such as (C₁-C₄)-dialkylamines, C₁-C₄)-trialkylamines, procaine, dibenzylamine, N,N'-dibenzylethylenediamine, N-benzyl-β-phenylethylamine, N-methylmorpholine or N-ethylmorpholine, 1-ephenamine, dihydroabietylamine, N,N,-bisdihydroabietylethylenediamine, N-lower alkyl piperidine and other amines which may be used for the formation of salts.

Surprisingly, the substituted 1,8-naphthyridines according to the invention show a superior inhibitory action on HMG-CoA reductase (3-hydroxy-3-methylglutarylcoenzyme A reductase).

In the context of the general formula (I), compounds of the general formula (Ia) and (Ib)

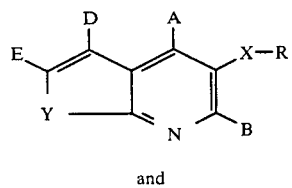

(Ia)

and

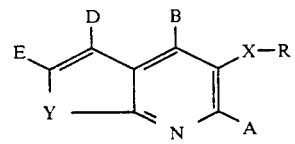

(Ib)

in which
A, B, D, E, X, Y and R¹ have the abovementioned meaning, are preferred.

Preferred compounds are those of the general formula (Ia) and (Ib),
in which
A
represents pyridyl or pyrimidyl, which is optionally monosubstituted or disubstituted by identical or different substituents from the series comprising fluorine, chlorine, bromine, trifluoromethyl, straight-chain or branched alkyl having up to 6 carbon atoms or phenyl, or A represents phenyl or naphthyl, which is optionally monosubstituted to tetrasubstituted by identical or different substituents from the series comprising straight-chain or branched alkyl, alkylthio, alkylsulphonyl, alkoxy or alkoxycarbonyl in each case having up to 8 carbon atoms, which may in turn be substituted by hydroxyl, alkoxy having up to 4 carbon atoms, phenyl or by a group of the formula -NR¹R²,
in which
R¹ and R² are identical or different and
denote hydrogen, phenyl, phenylsulphonyl, straight-chain or branched alkyl or alkylsulphonyl having up to 6 carbon atoms, benzyl or benzylsulphonyl, or
denote a group of the formula -COR³,
in which
R³
denotes straight-chain or branched alkyl or alkoxy having up to 6 carbon atoms or phenyl,
or the phenyl or naphthyl is optionally mono- to tetrasubstituted by is substituted by phenyl, phenyloxy, fluorine, chlorine, bromine, nitro, cyano, trifluoromethyl, trifluoromethoxy, benzyloxy or by a group of the formula -NR¹R²,
in which
R¹ and R² have the abovementioned meaning,
B
represents cyclopropyl, cyclobutyl, cyclopentyl or cyclohexyl,
represents straight-chain or branched alkyl having up to 10 carbon atoms, which may optionally be substituted by fluorine, chlorine, bromine, trifluoromethyl or methylthio,
D and E are identical or different and
represent hydrogen, hydroxyl, alkoxy having up to 6 carbon atoms, straight-chain or branched alkyl having up to 8 carbon atoms, phenyl or a group of the formula -NR¹R²,
in which
R¹ and R² have the abovementioned meaning,
Y
represents a group of the formula

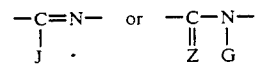

in which
J
denotes hydrogen, hydroxyl, mercapto, fluorine, chlorine or bromine, or denotes straight-chain or branched alkyl, alkoxy or alkylthio having up to 8 carbon atoms, which are optionally substituted by phenyl, or denotes phenoxy, benzyloxy or a group of the formula $-NR^1R^2$, in which
$R^1$ and $R^2$ have the abovementioned meaning, Z
denotes oxygen or sulphur, G
denotes hydrogen, straight-chain or branched alkyl or alkenyl in each case having up to 8 carbon atoms, which is optionally substituted by fluorine, chlorine, bromine, cyano, alkoxy having up to 6 carbon atoms, phenyl, phenoxy, benzyloxy, pyrryl, furyl or by a group of the formula $-NR^1R^2$, $-COR^3$ or $-COOR^4$, in which
$R^1$, $R^2$ and $R^3$ have the abovementioned meaning, $R^4$
denotes hydrogen, straight-chain or branched alkyl having up to 8 carbon atoms, which is optionally substituted by hydroxyl, phenyl, fluorine, chlorine or bromine, denotes phenyl which may in turn be substituted by fluorine, chlorine, bromine or hydroxyl, X
represents a group of the formula $-CH_2-CH_2-$ or $-CH=CH-$ and
R
represents a group of the formula $$-\underset{\underset{OH}{|}}{CH}-CH_2-\underset{\underset{OH}{|}}{\overset{\overset{R^5}{|}}{C}}-CH_2-COOR^6 \quad \text{or} \quad HO\underset{}{\overset{R^5}{\diagdown}}\!\!\diagup\!\!\diagdown\!\!\overset{O}{\diagup}\diagdown_O$$

in which
$R^5$
denotes hydrogen or straight-chain or branched alkyl having up to 8 carbon atoms and
$R^6$
denotes hydrogen or straight-chain or branched alkyl having up to 8 carbon atoms, or benzyl, or
denotes phenyl or a cation
and their salts.

Particularly preferred compounds of the general formulae (Ia) and (Ib) are those
in which
A
represents phenyl which is optionally monosubstituted to trisubstituted by identical or different substituents from the series comprising straight-chain or branched alkyl having up to 6 carbon atoms, which may in turn be substituted by hydroxyl, methoxy, ethoxy, propoxy or phenyl, or the phenyl is substituted by phenyl, phenoxy, fluorine, chlorine, bromine or benzyloxy, B
represents cyclopropyl, cyclobutyl, cyclopentyl or cyclohexyl,
represents methyl, ethyl, propyl, isopropyl, butyl, isobutyl, tert.butyl or trifluoromethyl, D and E are identical or different and represent hydrogen, hydroxyl, methyl, ethyl, propyl, isopropyl, methoxy or ethoxy, Y
represents a group of the formula $$-\underset{\underset{J}{|}}{C}=N- \quad \text{or} \quad -\underset{\underset{Z}{|}}{\overset{\overset{}{\|}}{C}}-\underset{\underset{G}{|}}{N}-$$

in which
J
denotes hydrogen, hydroxyl, fluorine or chlorine, or denotes straight-chain or branched alkyl, alkoxy or alkylthio having up to 6 carbon atoms, which are optionally substituted by phenyl, or denotes benzyloxy or a group of the formula $-NR^1R^2$, in which
$R^1$ and $R^2$ are identical or different and denote hydrogen or straight-chain or branched alkyl having up to 4 carbon atoms, or benzyl, Z
denotes oxygen or sulphur, G
denotes hydrogen, straight-chain or branched alkyl having up to 6 carbon atoms, which is optionally substituted by fluorine, chlorine, cyano, alkoxy having up to 4 carbon atoms, phenyl, benzyloxy or by a group of the formula $-COR^3$ or $-COOR^4$, in which
$R^3$
denotes straight-chain or branched alkyl or phenyl, $R^4$
denotes hydrogen, straight-chain or branched alkyl having up to 6 carbon atoms or phenyl, X
represents a group $-CH=CH-$ or $-CH_2-CH_2-$ and
R
represents a group of the formula $$-\underset{\underset{OH}{|}}{CH}-CH_2-\underset{\underset{OH}{|}}{\overset{\overset{R^5}{|}}{C}}-CH_2-COOR^6 \quad \text{or} \quad HO\underset{}{\overset{R^5}{\diagdown}}\!\!\diagup\!\!\diagdown\!\!\overset{O}{\diagup}\diagdown_O$$

in which
$R^5$
denotes hydrogen, methyl, ethyl, propyl, isopropyl, butyl, isobutyl or tert.butyl and
$R^6$
denotes hydrogen, methyl, ethyl, propyl, isopropyl, butyl, isobutyl, tert.butyl or benzyl, or
denotes a sodium, potassium, calcium, magnesium or ammonium ion and their salts.

The substituted 1,8-naphthyridines of the general formula (I) according to the invention have several asymmetric carbon atoms and can therefore exist in various stereochemical forms. The invention relates both to the individual isomers and to their mixtures.

Depending on the meaning of the group X or the radical R, different stereoisomers result, which are intended to be illustrated in more detail in the following:

a) if the group -X- represents a group of the formula $-CH=CH-$, the compounds according to the invention can exist in two stereoisomeric forms which can have the E configuration (II) or Z configuration (III) on the double bond:

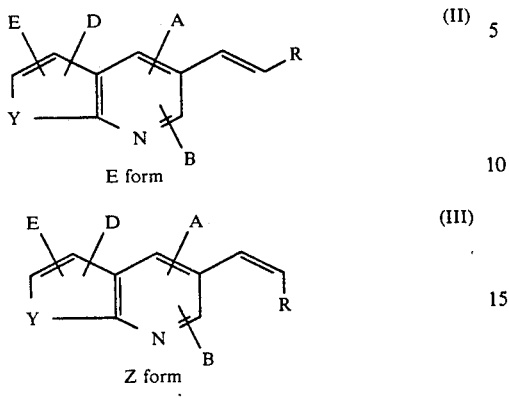

E form (II)

Z form (III)

(A, B, D, E and R have the abovementioned meaning).

Preferred compounds of the general formula (I) are those which have the E configuration (II).

b) If the radical -R- represents a group of the formula

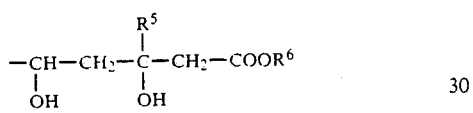
(formula numbered 30)

the compounds of the general formula (I) have at least two asymmetric carbon atoms, namely the two carbon atoms to which the hydroxyl groups are bonded. Depending on the relative position of these hydroxyl groups to one another, the compounds according to the invention may be present in the erythro configuration (IV) or in the threo configuration (V).

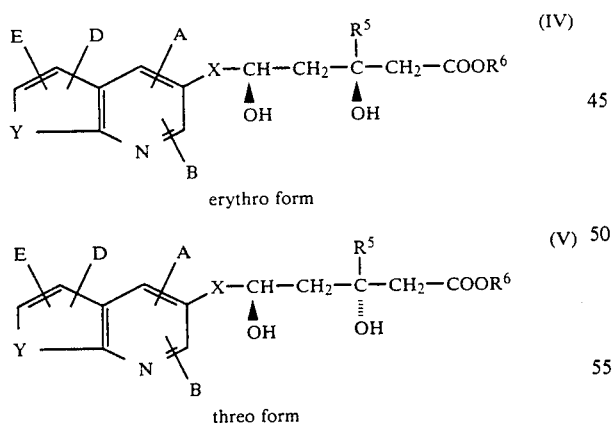

erythro form (IV)

threo form (V)

In turn, two enantiomers each exist both of the compounds in the erythro and in the threo configuration, namely the 3R,5S-isomer or the 3S,5R-isomer (erythro form) and the 3R,5R-isomer and 3S,5S-isomer (threo form).

In this connection, the isomers in the erythro configuration are preferred, particularly preferably the 3R,5S-isomer and the 3R,5S-3S,5R-racemate.

c) If the radical -R- represents a group of the formula

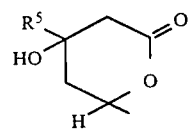

the substituted 1,8-naphthyridines have at least two asymmetric carbon atoms, namely the carbon atom to which the hydroxyl group is bonded, and the carbon atom to which the radical of the formula

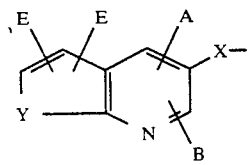

is bonded. Depending on the position of the hydroxyl group to the free valency on the lactone ring, the substituted 1,8-naphthyridines may be present as cis-lactones (VI) or as trans-lactones (VII).

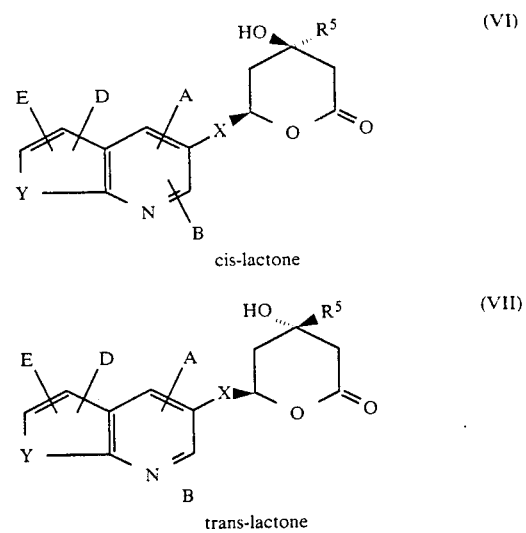

cis-lactone (VI)

trans-lactone (VII)

In turn, two isomers each exist of the cis-lactone and the trans-lactone, namely the 4R,6R-isomer or the 4S,6S-isomer (cis-lactone), and the 4R,6S-isomer or 4S,6R-isomer (trans-lactone). Preferred isomers are the trans-lactones. The 4R,6S-isomer (trans) and the 4R,6S-4S,6R-racemate are particularly preferred in this connection.

For example, the following isomeric forms of the substituted 1,8-naphthyridines may be mentioned:

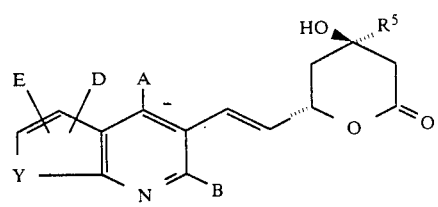

-continued

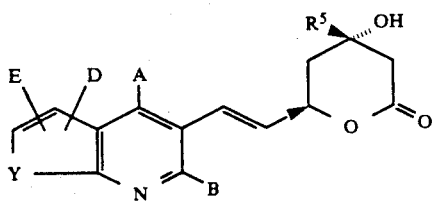
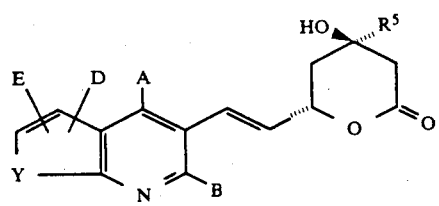
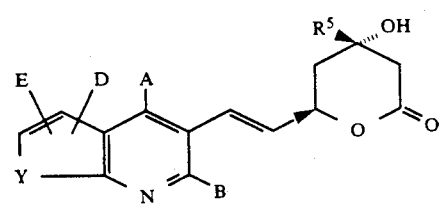
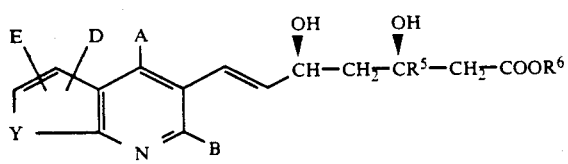
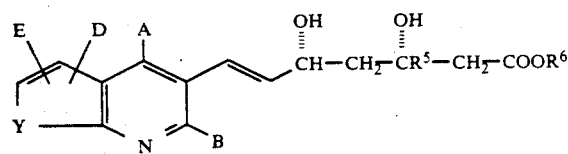
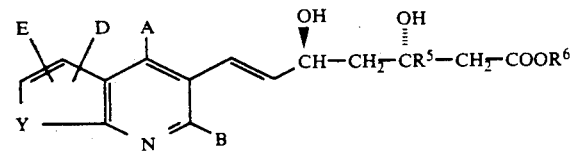
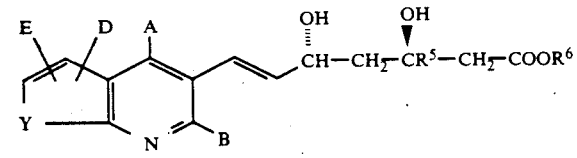
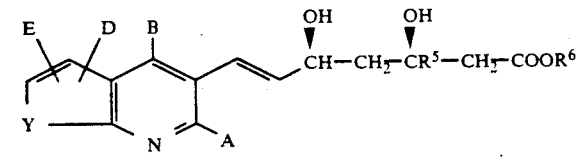

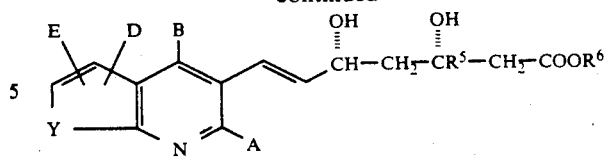
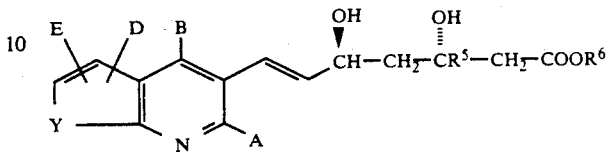
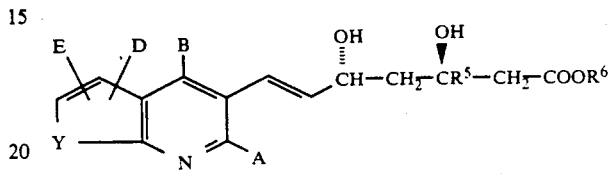

In addition, a process for the preparation of the substituted 1,8-naphthyridines of the general formula (I)

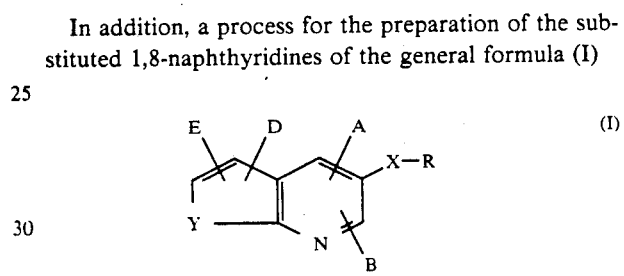

in which

A, B, D, E, X Y and R have the abovementioned meaning, has been found, which is characterized in that ketones of the general formula (VIII)

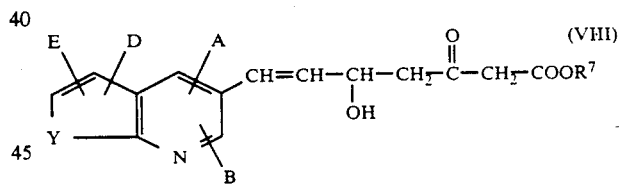

in which

A, B, D, E and Y have the abovementioned meaning, and $R^7$ represents alkyl, are reduced, in the case of the preparation of the acids the esters are hydrolyzed, in the case of the preparation of the lactones the carboxylic acids are cyclized, in the case of the preparation of the salts either the esters or the lactones are hydrolyzed, in the case of the preparation of the ethylene compounds (X=-CH$_2$-CH$_2$-) the ethene compounds (X=-CH=CH-) are hydrogenated according to customary methods, and, if appropriate, isomers are separated.

The process according to the invention can be illustrated by the following equation:

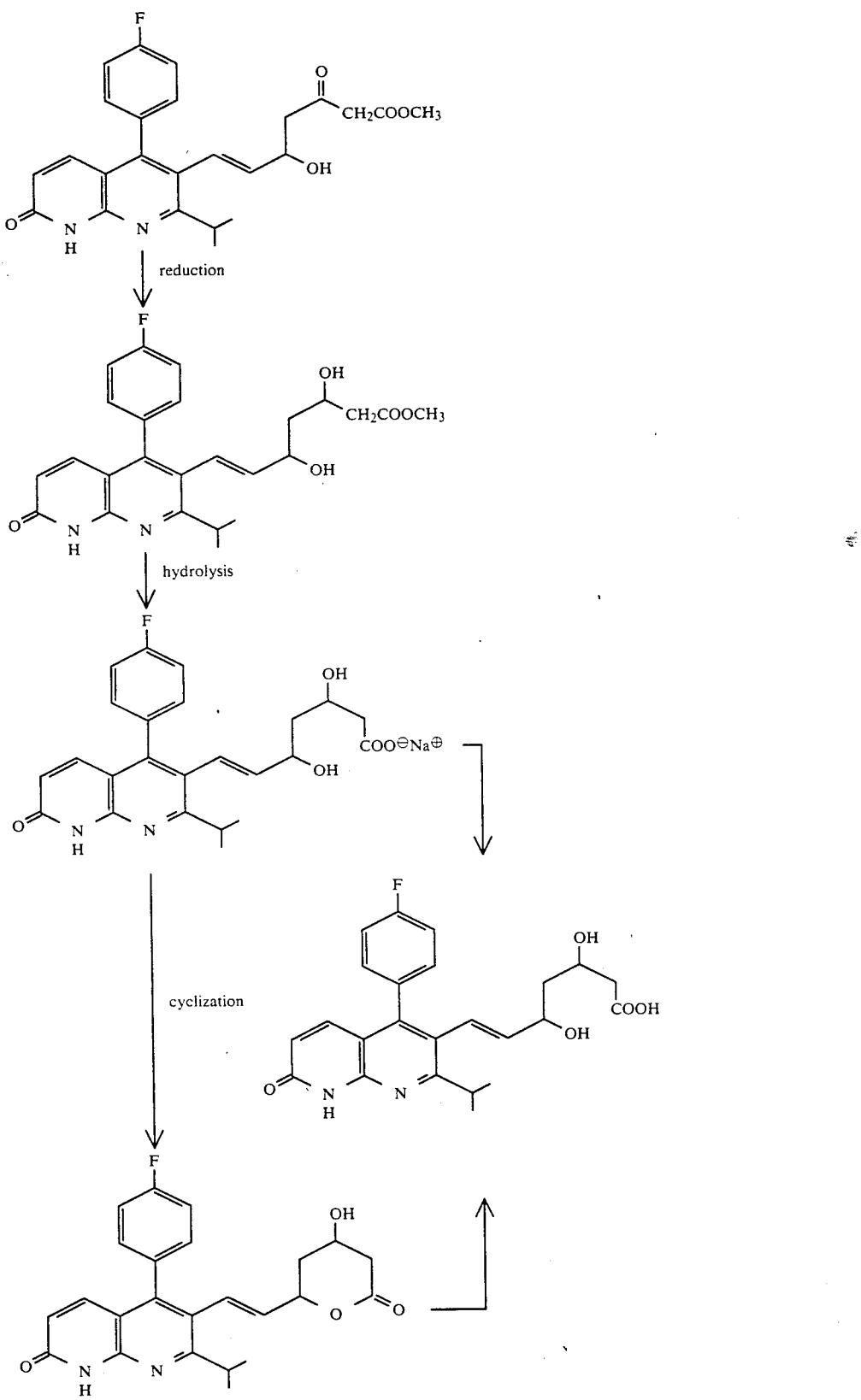

The reduction can be carried out using the customary reducing agents, preferably those which are suitable for the reduction of ketones to hydroxy compounds. Reduction using metal hydrides or complex metal hydrides in inert solvents is particularly suitable in this connection, if appropriate in the presence of a trialkylborane. Preferably, the reduction is carried out using complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminum hydride. Very particularly preferably, the reduction is carried out using sodium borohydride in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is likewise possible to employ mixtures of the solvents mentioned.

Particularly preferably, the reduction of the ketone group to the hydroxyl group is carried out under conditions in which the customary functional groups such as, for example, the alkoxycarbonyl group do not change. The use of sodium borohydride as a reducing agent in the presence of triethylborane in inert solvents such as, preferably, ethers is particularly suitable for this purpose.

The reduction is in general carried out in a temperature range from $-80°$ C. to $+30°$ C., preferably from $-78°$ C. to $0°$ C.

The process according to the invention is in general carried out at atmospheric pressure. However, it is also possible to carry out the process at reduced pressure or at elevated pressure (for example in a range from 0.5 to 5 bar).

In general, the reducing agent is employed in an amount from 1 to 2 moles, preferably from 1 to 1.5 moles, relative to 1 mole of the keto compound.

Under the abovementioned reaction conditions, the carbonyl group is in general reduced to the hydroxyl group without reduction of the double bond to a single bond taking place.

In order to prepare compounds of the general formula (I), in which X represents an ethylene grouping, the reduction of the ketones (III) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ic)

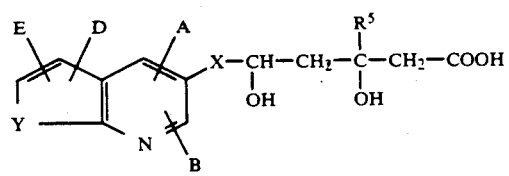

in which
  A, B, D, E, and $R^1$ have the abovementioned meaning.

The carboxylic acid esters in the context of the general formula (I) correspond to the formula (Id)

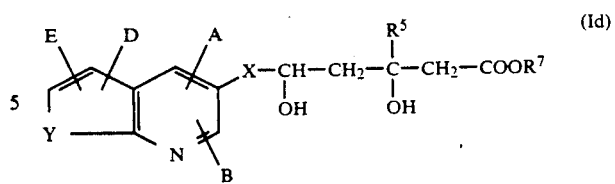

in which
  A, B, D, E, Y and $R^5$ have the abovementioned meaning, and
  $R^7$ represents alkyl.

The salts of the compounds in the context of the general formula (I) according to the invention correspond to the formula (Ie)

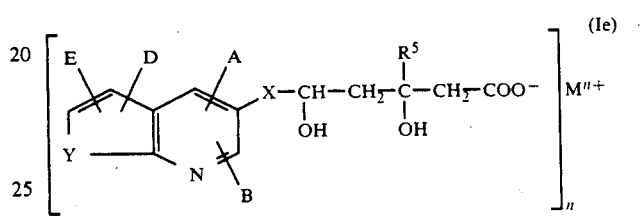

in which
  A, B, D, E, Y and $R^1$ have the abovementioned meaning, and
  $M^{n+}$ represents a cation, where n indicates the valency.

The lactones in the context of the general formula (I) correspond to the formula (If)

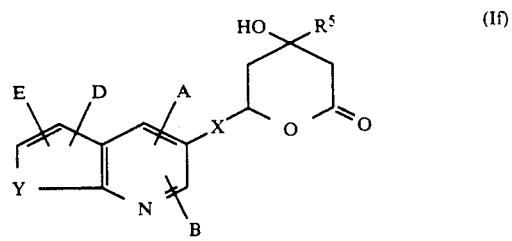

in which
  A, B, D, E, Y and $R^5$ have the abovementioned meaning.

In order to prepare the carboxylic acids of the general formula (Ic) according to the invention, the carboxylic acid esters of the general formula (Id) or the lactones of the general formula (If) are in general hydrolyzed according to customary methods. Hydrolysis is in general carried out by treating the esters or the lactones in inert solvents with customary bases, in general the salts of the general formula (Ie) initially resulting, which can subsequently be converted in a second step by treating with acid into the free acids of the general formula (Ic).

Suitable bases for hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert. butoxide.

Sodium hydroxide or potassium hydroxide are particularly preferably employed.

Suitable solvents for hydrolysis are water or the organic solvents customary for hydrolysis. These preferably include water, alcohols such as methanol, ethanol, propanol, isopropanol or butanol, or ethers such as tetrahydrofuran or dioxane, or dimethylformamide or dimethyl sulphoxide. Particularly preferably, methanol, tetrahydrofuran or water are used. It is also possible to employ mixtures of the solvents mentioned.

The hydrolysis is in general carried out in a temperature range from 0° C. to +100° C., preferably from +20° C. to +80° C.

In general, the hydrolysis is carried out at atmospheric pressure. However, it is also possible to work at reduced pressure or elevated pressure (for example from 0.5 to 5 bar).

When carrying out the hydrolysis, the base is in general employed in an amount from 1 to 3 moles, preferably from 1 to 1.5 moles, relative to 1 mole of the ester or the lactone. Molar amounts of the reactants are particularly preferably used.

When carrying out the reaction, the salts of the compounds (Ie) according to the invention are formed in the first step as intermediates which can be isolated. The acids (Ic) according to the invention are obtained by treating the salts (Ie) with customary inorganic acids. These preferably include mineral acids such as, for example, hydrochloric acid, hydrobromic acid, sulphuric acid or phosphoric acid. It has proved advantageous in this connection in the preparation of the carboxylic acids (Ic) to acidify the basic reaction mixture from the hydrolysis in a second step without isolation of the salts. The acids can then be isolated in a customary manner.

In order to prepare the lactones of the formula (If) according to the invention, the carboxylic acids (Ic) according to the invention are in general cyclized according to customary methods, for example by heating the corresponding acid in inert organic solvents, if appropriate in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of the solvents mentioned. Hydrocarbons, in particular toluene, in the presence of molecular sieve are particularly preferably used.

The cyclization is in general carried out in a temperature range from −40° C. to +200° C., preferably from −25° C. to +50° C.

The cyclization is in general carried out at atmospheric pressure, but it is also possible to carry out the process at reduced pressure or at elevated pressure (for example in a range from 0.5 to 5 bar).

Moreover, the cyclization is also carried out in inert organic solvents, with the aid of cyclizing or dehydrating agents. Carbodiimides are preferably used as dehydrating agents in this connection. N,N'-dicyclohexylcarbodiimide paratoluenesulphonate, N-cyclohexyl-N'-[2-(N''-methylmorpholinium)ethyl]carbodiimide or N-(3-di-methylaminopropyl)-N'-ethylcarbodiimide hydrochloride are preferably employed as carbodiimides Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene, xylene or mineral oil fractions are particularly preferred. Chlorinated hydrocarbons such as, for example, methylene chloride, chloroform or carbon tetrachloride are particularly preferably employed.

The reaction is in general carried out in a temperature range from 0° C. to +80° C., preferably from +10° C. to +50° C.

When carrying out the cyclization, it has proved advantageous to employ the cyclization method with the aid of carbodiimides as dehydrating agents.

The resolution of the isomers into the stereoisomerically uniform constituents is in general carried out by customary methods such as are described, for example, by E.L. Eliel, Stereochemistry of Carbon Compounds, McGraw Hill, 1962. Resolution of the isomers in the racemic ester step is preferred in this connection. The racemic mixture of the trans-lactones (VII) is particularly preferably converted in this case by treating either with D-(+)- or L-(−)-α-methylbenzylamine by customary methods into the diastereomeric dihydroxyamides (Ig)

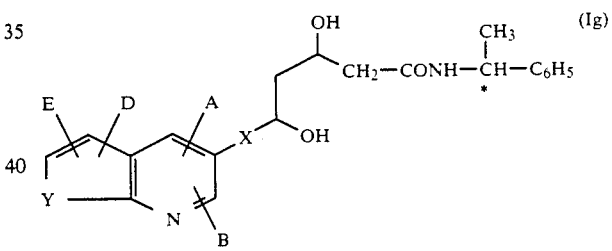

which can then be resolved into the individual diastereomers as is customary by chromatography or crystallization. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, gives the corresponding enantiomerically pure dihydroxy acids (Ic) which can be converted into the enantiomerically pure lactones by cyclization as described above. In general, it is true for the preparation of the compounds of the general formula (I) according to the invention in enantiomerically pure form that the configuration of the final products according to the method described above is dependent on the configuration of the starting substances.

The resolution of isomers is intended to be illustrated by way of example in the following scheme:

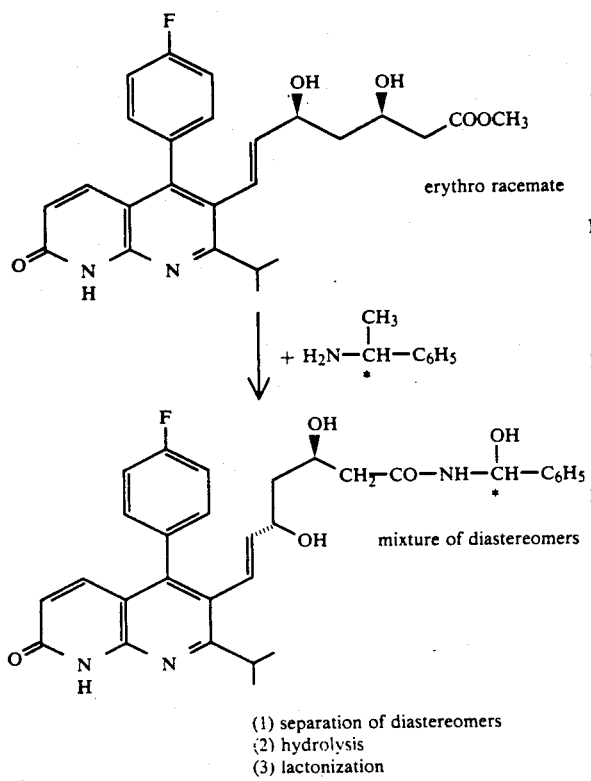

erythro racemate $+ H_2N-\overset{CH_3}{\underset{*}{CH}}-C_6H_5$ mixture of diastereomers (1) separation of diastereomers
(2) hydrolysis
(3) lactonization

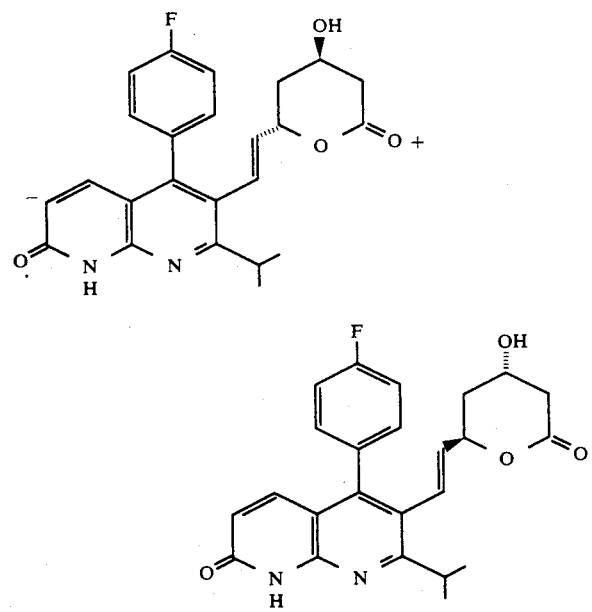

The ketones (VIII) employed as starting substances are new.

A process for the preparation of the ketones of the general formula (VIII) according to the invention

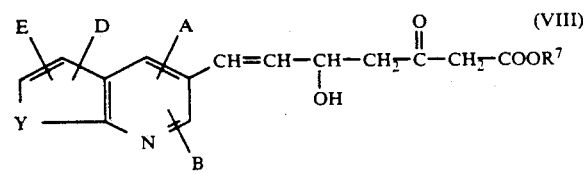

in which

A, B, D, E, Y and $R^7$ have the abovementioned meaning, has been found, which is characterized in that aldehydes of the general formula (IX)

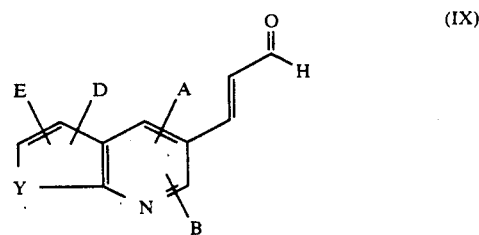

in which

A, B, D, E and Y have the abovementioned meaning, are reacted in inert solvents with acetoacetic esters of the general formula (X)

in which $R^7$ has the abovementioned meaning, in the presence of bases.

The process according to the invention can be illustrated, for example, by the following equation:

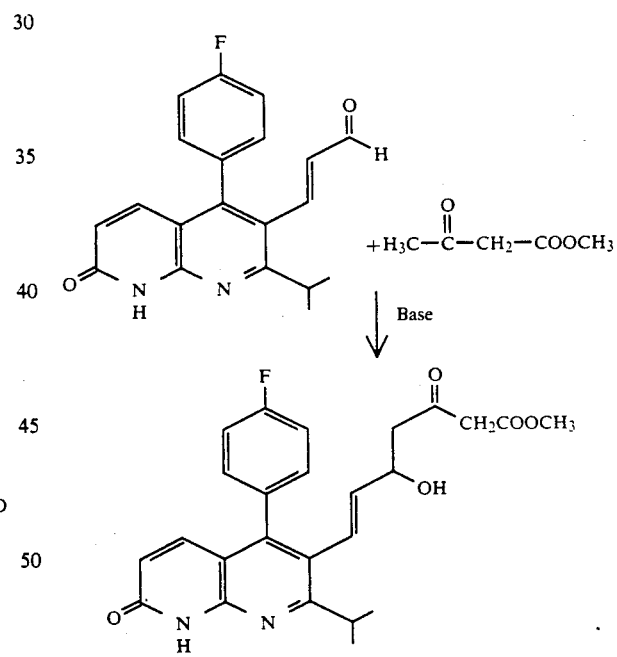

Suitable bases in this connection are the customary strong basic compounds. These preferably include organolithium compounds such as, for example, N-butyl lithium, sec. butyllithium, tert. butyllithium or phenyl lithium, or amides such as, for example, lithium diisopropylamide, sodium amide or potassium amide, or lithium hexamethyldisilylamide, or alkali metal hydrides such as sodium hydride or potassium hydride. It is likewise possible to employ mixtures of the bases mentioned. N-butyllithium or sodium hydride or a mixture thereof is particularly preferably employed.

Additions of metal halides such as, for example, magnesium chloride, zinc chloride or zinc bromide may be advantageous. The addition of zinc halides is particularly preferred.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is likewise possible to employ mixtures of the solvents mentioned. Ethers such as diethyl ether or tetrahydrofuran are particularly preferably used.

The reaction is in general carried out in a temperature range from $-80°$ C. to $+50°$ C., preferably from $-20°$ C. to room temperature.

The process is in general carried out at atmospheric pressure, but it is also possible to carry out the process at reduced pressure or elevated pressure, for example in a range from 0.5 to 5 bar.

When carrying out the process, the acetoacetic ester is in general employed in an amount from 1 to 5, preferably from 1 to 3, moles, relative to 1 mole of the aldehyde.

The acetoacetic esters of the formula (X) employed as starting substances are known or can be prepared by known methods [Beilstein's Handbuch der organischen Chemie (Beilstein's Handbook of Organic Chemistry) III, 632; 438].

Examples of acetoacetic esters for the process according to the invention which may be mentioned are: methyl acetoacetate, ethyl acetoacetate, propyl acetoacetate and isopropyl acetoacetate.

The preparation of the aldehydes of the general formula (IX) employed as starting substances is intended to be illustrated below by way of example for the 1,8-naphthyridines of the type (Ia).

In this connection, according to scheme A, 1,8-naphthyridines of the formula (XI), in which $R^8$ represents an alkyl radical having up to 4 carbon atoms, are reduced to the hydroxymethyl compounds (XII) in the first step [1] in inert solvents such as ethers, for example diethylether, tetrahydrofuran or dioxane or hydrocarbons such as toluene, preferably toluene, using metal hydrides as reducing agents, for example lithium aluminum hydride, sodium cyanoborohydride, sodium aluminum hydride, diisobutylaluminum hydride or sodium bis(2-methoxyethoxy)-dihydroaluminate, in temperature ranges from $-75°$ C. to $+100°$ C., preferably from $-80°$ C. to room temperature, or from room temperature to $-78°$ C. depending on the reducing agent used. Preferably, the reduction is carried out using diisobutylaluminum hydride in tetrahydrofuran or toluene in a temperature range from $-78°$ C. to room temperature. The hydroxymethyl compounds (XII) are oxidized by customary methods to the aldehydes (XIII) in the second step [2]. The oxidation can be carried out, for example, with pyridinium chlorochromate, if appropriate in the presence of alumina, in inert solvents such as chlorinated hydrocarbons, preferably methylene chloride, in a temperature range from $0°$ C. to $60°$ C., preferably at room temperature, or else are carried out using dimethyl sulphoxide by the customary methods of Swern oxidation. The aldehydes (XIII) are reacted to give the aldehydes (IX) in the third step [3] using diethyl-2-(cyclohexyl-amino)-vinylphosphonate in the presence of sodium hydride in inert solvents such as ethers, for example diethylether, tetrahydrofuran or dioxane, preferably in tetrahydrofuran, in a temperature range from $-20°$ C. to $+40°$ C., preferably from $-5°$ C. to room temperature.

The 1,8-naphthyridines of the formula (XI) employed as starting substances in this connection are new.

Compounds of the formula (XIa), in which Y represents the group of the formula $$-\underset{Z}{\overset{\|}{C}}-\underset{G}{\overset{|}{N}}-$$

in which

G and Z have the abovementioned meaning, can be obtained by oxidizing 3,4-dihydro-1,8-naphthyridines of the formula (XIV), in which A, B, D, E, G, Z and $R^8$ have the abovementioned meaning, according to scheme [B]. The oxidation can carried out, for example, with chromic oxide or sodium nitrite in glacial acetic acid, with nitric acid in a aqueous suspension, with cerium salts such as, for example, ammonium cerium nitrate in a solvent mixture of acetonitrile and water, or with dichlorodicyano-p-benzoquinone in the abovementioned inert solvents, in a temperature range from $-20°$ C. to $150°$ C.

[A]

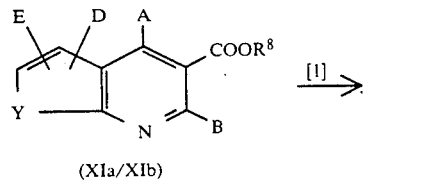

(XIa/XIb)

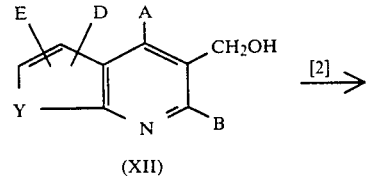

(XII)

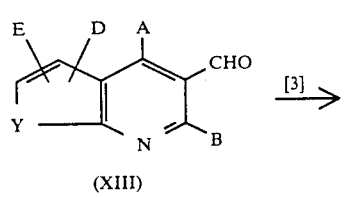

(XIII)

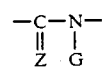

(IX)

[B]

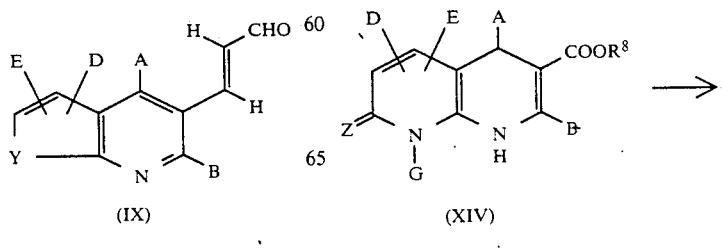

(XIV)

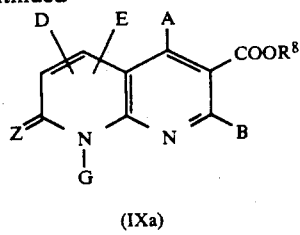

(IXa)

The 3,4-dihydro-1,8-naphthyridines of the general formula (XIV) employed as starting substances in this connection are new.

They are obtained according to scheme [C] by reaction of suitably substituted α,β-unsaturated carboxylic acid esters of the general formula (XV), in which A, B and $R^8$ have the abovementioned meaning, with substituted 6-amino-2-pyridones of the general formula (XVI), in which D, E, G and Z have the abovementioned meaning.

The reaction can be illustrated by the following equation

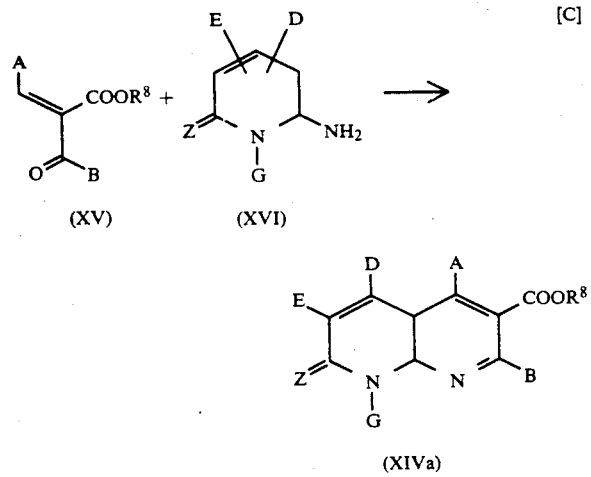

The process can be carried out in substance or in a high-boiling solvent such as, for example, ethylene glycol or dimethylformamide, if appropriate in the presence of acetic acid, at room temperature to +200° C. Reaction in substance or dimethylformamide at +120° C. to +160° C. is preferred In addition, compounds of the general formula (I) in which Y represents the group of the formula

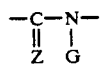

and G denotes a $C_1$–$C_{S6}$-alkyl radical, can be prepared by alkylating compounds of the general formulae (XIII), (XIV) or (I), in which G represents hydrogen, with $C_1$–$C_6$-alkyl halides, such as, for example, methyl iodide in the presence of bases, such as, for example, potassium tert.butoxide, in the abovementioned solvents, preferably in dimethylformamide at room temperature.

Compounds of the formula (XIb), in which Y represents the group of the formula

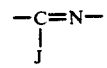

in which J has the abovementioned meaning, can be prepared by reacting compounds of the formula (XIa) by methods known from the literature [cf. L.F. Fieser, M. Fieser, Reagents for Organic Synthesis, Vo. 1, . 1232 (1967)] either with trialkyloxonium salts, preferably with trimethyloxonium tetrafluoroborohy,iride at room temperature, or with bases such as, for example, potassium tert.butoxide or sodium hydride and $C_1$–$C_6$-alkyl halides such as, for example, methyl iodide, ethyl iodide or isopropyl iodide, preferably with isopropyl iodide, in the abovementioned solvents at room temperature. It is also possible first to carry out a chlorination reaction with phosphorus chlorides, such as, for example, phosphorus oxychloride, in the presence of $C_1$–$C_4$-dialkylanilines at 0° C. to +100° C. and then to introduce the group F by nucleophilic substitution.

The compounds of the general formula (I) according to the invention possess useful pharmacological properties and can be employed in medicaments. In particular, they are inhibitors of 3-hydroxy-3-methylglutaryl-coenzyme A (HMG-CoA) reductase and, as a result of this, inhibitors of cholesterol biosynthesis. They can therefore be employed for the treatment of hyperlipoproteinaemia, lipoproteinaemia or atherosclerosis. The active substances according to the invention additionally cause a lowering of the cholesterol content in the blood.

The enzyme activity determination was carried out as modified by G.C. Ness et al., Archives of Biochemistry and Biophysics 197, 493–499 [1979]. Male Rico rats (body weight 300–400 g) were treated for 11 days with altromin powdered feed to which 40 g of cholestyramine/kg of feed had been added. After decapitation, the liver was removed from the animals and placed on ice. The livers were comminuted and homogenized 3 times in 3 volumes of 0.1 M sucrose, 0.05 M KCl, 0.04 M $K_xH_y$ phosphate, 0.03 M ethylenediaminetetraacetic acid, 0.002 m dithiothreitol [SPE] buffer pH 7.2 in a Potter-Elvejem homogenizer. The mixture was then centrifuged at 15,000 g for 15 minutes and the sediment was discarded. The supernatant was sedimented at 100,000 g for 75 minutes. The pellet is taken up in ¼ volumes of SPE buffer, homogenized once more and then centrifuged again at 100,000 g for 60 minutes. The pellet is taken up using a 5-fold amount of its volume of SPE buffer, homogenized and frozen and stored at −78° C. (=enzyme solution).

For testing, the test compounds (or mevinolin as a reference substance) were dissolved in dimethylformamide with the addition of 5 vol.-% of 1 N NaOH and, using 10 μl, employed in the enzyme test in various concentrations. The test was started after preincubation of the compounds with the enzyme at 37° C. for 20 minutes. The test batch was 0.380 ml and contained 4 μmol of glucose-6-phosphate, 1.1 mg of bovine serum albumin, 2.1 μmol of dithiothreitol, 0.35 μmol of NADP, 1 unit of glucose-6-phosphate dehydrogenase, 35 μmol of $K_xH_y$ phosphate pH 7.2, 20 μl of enzyme preparation and 56 nmol of 3-hydroxy-3-methyl-glutaryl-coenzyme A (glutaryl-3-$^{14}$C) 100,000 dpm.

After incubating for 60 minutes at 37° C., the batch was centrifuged and 600 μl of the supernatant was applied to a 0.7×4 cm column packed with a 5-chloride 100-200 mesh (anion exchanger). The column was subsequently washed with 2 ml of distd. water and 3 ml of Aquasol were added to runnings plus washing water and counted in an LKB scintillation counter. IC$_{50}$ values were determined by intrapolation by plotting the percentage inhibition against the concentration of the compound in the test. In order to determine the relative inhibitory potency, the IC$_{50}$ value of the reference substance mevinolin was set at 1 and compared with the simultaneously determined IC$_{50}$ value of the test compound.

The new active substances can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, if appropriate organic solvents can be used as auxiliary solvents.

Examples of auxiliaries which may be mentioned are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, clays, talc, chalk), ground synthetic minerals (for example highly disperse silica, silicates), sugars (for example sucrose, lactose and dextrose), emulsifiers (for example polyoxyethylene fatty acid esters, polyoxyethylene ethylene fatty alcohol ethers, alkylsulphonates and arylsulphonates), dispersing agents (for example ligninsulphite waste liquors, methylcellulose, starch and polyvinylpyrrolidone) and lubricants (for example magnesium stearate, talc, stearic acid and sodium lauryl sulphate).

Administration is carried out in a customary manner, preferably orally, parenterally, perlingually or intravenously. In the case of oral administration, tablets may of course also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tableting. In the case of aqueous suspensions, various flavor enhancers or colorants may be added to the active compounds in addition to the above-mentioned auxiliaries.

In the case of parenteral administration, solutions of the active compounds using suitable liquid excipients may be employed.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this it may be necessary to deviate from the amounts mentioned, depending on the body weight or the type of administration route, on individual behavior towards the medicament, the manner of its formulation and the point in time or interval at which administration takes place.

Thus in some cases it may be sufficient to manage with less than the minimum amount previously mentioned, whereas in other cases the upper limit mentioned must be exceeded. In the case of the administration of larger amounts, it may be advisable to divide these into a number of individual doses over the day.

PREPARATION EXAMPLES

EXAMPLE 1

E,Z-2-Ethoxycarbonyl-1-(4-fluorophenyl)-4-methyl-pent-1-en-3-one

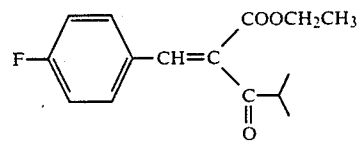

A solution of 20 ml (0.2 mol) of piperidine and 12 ml (0.21 mmol) of acetic acid in 200 ml of isopropanol is added to 554 g (3.5 mol) of ethyl isobutyryl acetate and 434 g (3.5 mol) of 4-fluorobenzaldehyde- in 1.8 l of isopropanol. The mixture is stirred at room temperature for 1 day and concentrated in vacuo. and the residue is distilled in a high vacuum.

Yield: 796 g (86% of theory) of yellowish oil
b.p. 135-140° C. (0.2 mbar)

EXAMPLE 2

6-Ethoxycarbonyl-5-(4-fluorophenyl)-1,2-dihydro-7-iso-propyl-2-oxo-1,8-naphthyridine

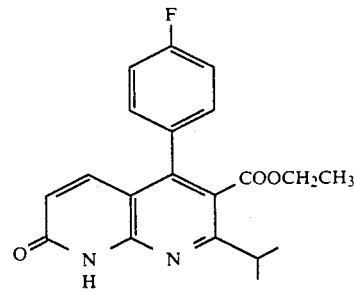

66 g (0.6 mol) of 6-amino-pyridin-2-one [0.A. Seide, A.I. Titow, Ber. dtsch. Chem. Ges. 69, 1884 (1936)] and 159 g (0.6 mol) of the compound from Example 1 are stirred at 100° C. for 3 h in 50 ml of dimethylformamide. All volatile constituents are then distilled off up to a bath temperature of 200° C. and a pressure of 0.3 mbar. The dark residue is filtered through 1 kg of silica gel using chloroform and chloroform/methanol (10:1). After stripping off the solvent, a brown foam (60 g) remains.

This crude product is dissolved in 0.7 l of dichloromethane, 39.7 g (0.175 mol) of dichloro-dicyano-p-benzoquinone are added and the mixture is stirred at room temperature for 1 h. After filtering off the precipitate with suction from the reaction mixture and concentrating the filtrate, a residue remains which is filtered through 1 kg of silica gel using petroleum ether/ethyl acetate (5:1) to (2:1). The residue obtained from the filtrate is recrystallized from ethyl acetate/ether.

Yield: 21.7 g (10% of theory) of colorless crystals
m p.: 182° C.

EXAMPLE 3

(4-Fluorophenyl)-1,2-dihydro-6-hydroxy-methyl-7-isopropyl-2-oxo-1,8-naphthyridine

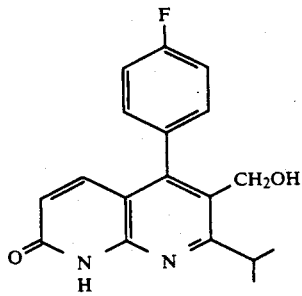

200 ml of a 1.5 molar solution of diisobutyl aluminum hydride in toluene are added dropwise at −78° C. during the course of 2 h to a solution of 21.7 g (61 mmol) of the compound from Example 2 in 700 ml of anhydrous toluene and the mixture is stirred for a further hour at this temperature. It is then allowed to warm slowly to room temperature, during which 200 ml of water are cautiously added dropwise. The mixture is filtered off with suction through Kieselguhr and washed with ethyl acetate, and the Kieselguhr is boiled again with ethyl acetate. The organic phase is washed with sodium chloride solution, dried over sodium sulphate and concentrated to dryness and the residue is crystallized from ethyl acetate/ether.

Yield: 18.8 g (97% of theory) of colorless crystals m.p.: 230° C. (from ethyl acetate)

EXAMPLE 4

5-(4-Fluorophenyl)-6-formyl-1,2-dihydro-7-isopropyl-2-oxo-1,8-naphthyridine

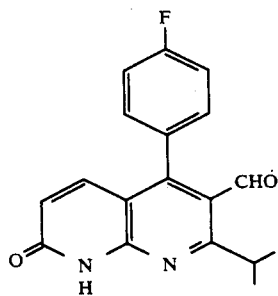

12.3 g of alumina and 25.9 g (120 mmol) of pyridinium chlorochromate are added to a solution of 18.8 g (60 mmol) of the compound from Example 3 in 300 ml of tetrahydrofuran and the mixture is stirred at room temperature for 1 h. It is filtered through 500 g of silica gel and washed with 1 l each of dichloromethane, petroleum ether/ethyl acetate (1:1) and ethyl acetate. The filtrate is concentrated on a rotary evaporator and the residue is crystallized from methanol.

Yield: 13.3 g (71% of theory) of colorless crystals m.p.: 223° C.

EXAMPLE 5

(E)-3-[5-(4-Fluorophenyl)-1,2-dihydro-7-isopropyl-2-oxo1, 8-naphthyridin-6-yl]-prop-2-enal

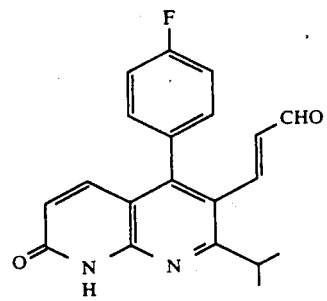

A solution of 13.1 g (50 mmol) of diethyl 2-(cyclohexylamino)-vinyl-phosphonate in 80 ml of tetrahydrofuran is added dropwise at 0° C. under argon to a suspension of 3.0 g (100 mmol) of 80% strength sodium hydride in 80 ml of anhydrous tetrahydrofuran and the mixture is stirred at this temperature for 30 min. A solution of 13.0 g (42 mmol) of the compound from Example 4 in 80 ml of tetrahydrofuran is then added dropwise at 0° C.−5° C. and the mixture is then heated under reflux for 1 h. 200 ml of water are added cautiously and the mixture is extracted three times with ethyl acetate. After concentrating the organic phases, the residue is heated under reflux for 2 h with a mixture of 500 ml of toluene, 500 ml of water and 27.5 g (218 mmol) of oxalic acid dihydrate. The toluene phase is concentrated and the residue is treated with ethyl acetate. 11.35 g (80% of theory) of colorless crystals of m.p. 261° C. are obtained.

EXAMPLE 6

Methyl erythro-(E)-7-[5-(4-fluorophenyl)-1,2-dihydro-7-isopropyl-2-oxo-1,8-naphthyridin-6]-3,5-dihydroxy-hept-6-enoate

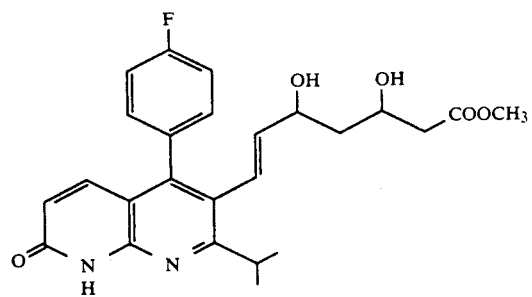

5.47 g (50.7 mmol) of methyl acetoacetate in 5 ml of tetrahydrofuran are added dropwise at −5° C. to 0° C. under argon to a suspension of 1.69 g (56.4 mmol) of 80% strength sodium hydride in 50 ml of anhydrous tetrahydrofuran. After 15 min, 41 ml (67.6 mmol) of 15% strength butyl lithium in hexane are added dropwise at the same temperature and, after a further 15 min, a solution of 5.68 g (16.9 mmol) of the compound from Example 5 in 150 ml of tetrahydrofuran. The mixture is stirred at room temperature for one hour, then 11.2 g of acetic acid in 120 ml of water are cautiously added dropwise and the mixture is extracted three times with ethyl acetate. The organic phases are washed with saturated sodium hydrogen carbonate and sodium chloride solution, dried over sodium sulphate and concentrated. 7.8 g of crude methyl-(E)-7[5-(4-fluorophenyl)1,2-dihydro-7-isopropyl-2-oxo-1,8-naphthyridin-6-yl]-5-hydroxy-3-oxo-hept-6-enoate are obtained as orange oil.

This crude product is dissolved under argon in 100 ml of anhydrous tetrahydrofuran, 20.3 ml of a 1 M solution of triethylborane in tetrahydrofuran are added and air is passed through the solution for 5 min. The mixture is cooled to −78° C., 767 mg (20.3 mmol) of sodium borohydride are added, then 11 ml of methanol are slowly added dropwise and the mixture is stirred for a further hour at −78° C. to −75° C. The mixture is then allowed to warm to room temperature, 53 ml of 30% strength hydrogen peroxide and 50 ml of water being added dropwise from about −30° C. The mixture is extracted three times with ethyl acetate, and the organic phases are dried over sodium sulphate and concentrated. The residue is chromatographed on 120 g of silica gel (230-400 mesh) using ethyl acetate/petroleum ether (2:1) to (4:1). A colorless foam (4.09 g) is obtained, which is recrystallized from methanol/water.

Yield: 2.32 g (30% of theory) of colourless crystals m.p.: 148° C.

EXAMPLE 7

Sodium erythro-(E)-7-[5-(4-fluorophenyl)-1,2-dihydro-7-isopropyl-2-oxo-1,8-naphthyridin-6-yl]-3,5-dihydroxy-hept-6-ene-carboxylate

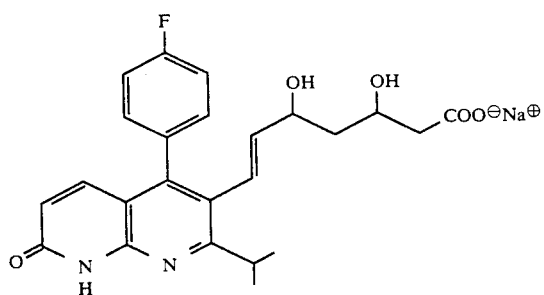

100 mg (0.22 mol) of the compound from Example 6 are stirred at room temperature for 1 h in 2.2 ml of tetrahydrofuran and 2.2 ml of 0.1 N sodium hydroxide solution. The solvent is stripped off and the residue is dried over phosphorus pentoxide in a high vacuum.

Yield: 85 mg of colorless crystals m.p.: from 170° C. (dec.)

EXAMPLE 8

Methyl erythro-(E)-7-[5-(4-fluorophenyl)-1,2-dihydro-7-isopropyl-1-methyl-2-oxo-1, 8naphthyridin-6-yl]3,5-dihydroxy-hept-6-enoate

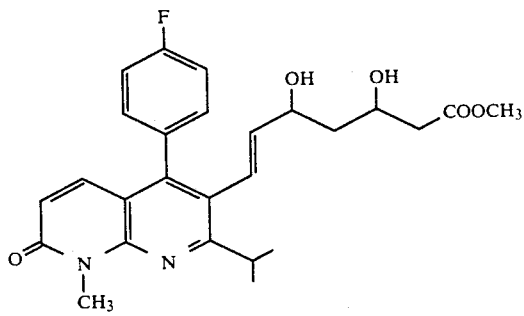

A solution of 275 mg (0.6 mol) of the compound from Example 6 in 5 ml of dimethylformamide and 86 mg (0.6 mol) of methyl iodide are added to a solution of 69 mg (0.6 mmol) of potassium tert.-butoxide in 5 ml of dimethylformamide and the mixture is stirred at room temperature for 4 h. A further 138 mg (1.2 mmol) of potassium tert.-butoxide and 344 mg (2.4 mmol) of methyl iodide are then added and the mixture is stirred overnight. The mixture is poured into water and extracted three times with ethyl acetate, and the organic phase is dried and concentrated (0.28 g of yellow oil). Column chromatography on 20 g of silica gel (230-400 mesh) using petroleum ether/ethyl acetate (1:1) and ethyl acetate gives 52 mg (18% of theory) of a colorless oil.

$^1$H-NMR (CDCl$_3$): δ=1.25-1.45 (m, 8H, CH(CH$_3$)$_2$+4-H); 2.45 (m, 2-H, 2-H); 3.07 (d, 1H, OH); 3.45 (sept, 1H, CH(CH$_3$)$_2$); 3.53 (d, 1H, OH); 3.72 (s, 3H; O-CH$_3$); 3.9 (s, 3H, N-CH$_3$); 4.1 (m, 1H, C-H); 4.35 (m, 1H, C-H); 5.3 (dd, 1H, 6-H); 6.43 (d, 1H, 7-H); 6.6 (d, 1H, 3'-H); 7.13 (m, 4H, aromatic-H); 7.28 (d, 1H, 4'-H) ppm.

EXAMPLE 9

(E)-3-[1-Ethyl-5-(4-fluorophenyl)-1,2-dihydro-7-isopropyl-2-oxo-1, 8-naphthyridin-6-yl]-prop-2-enal

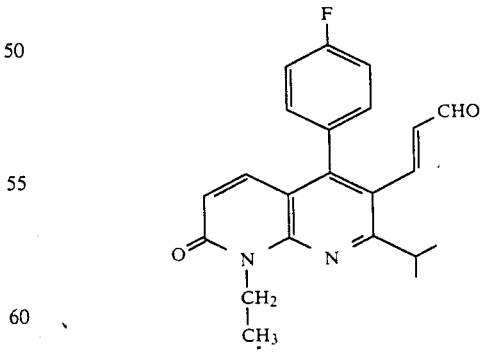

1.0 g (3 mmol) of the compound from Example 5 are suspended in 20 ml of dimethylformamide and a solution of 366 mg (3.3 mmol) of potassium tert.-butoxide in 5 ml of dimethylformamide and 510 mg (3.3 mmol) of ethyl iodide in 1 ml of dimethylformamide are successively added dropwise. The mixture is stirred at 60° C.

for 90 min, poured into 150 ml of ice water and extracted three times with ethyl acetate. The organic phases are dried and concentrated, and the residue is chromatographed on 30 g of silica gel (230-400 mesh, column diameter 2.5 cm) using petroleum ether/ethyl acetate (5:1) and (3:1).

Yield: 850 mg (78%), colorless crystals of melting point: 123° C.

In analogy to Example 9 are prepared starting from the compound of Example 5:

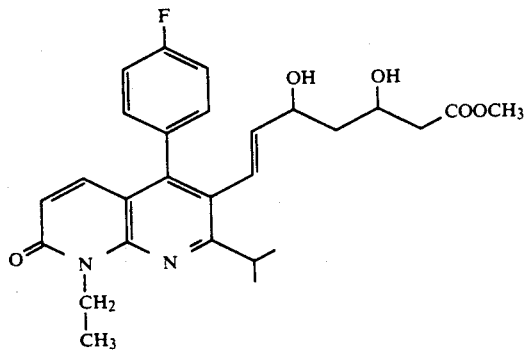

| No. Example | R | Reagent | m.p. | Yield |
|---|---|---|---|---|
| 10 | CH$_2$—C$_6$H$_5$ | Br—CH$_2$—C$_6$H$_5$ | 164 | 83% |
| 11 | —CH(CH$_3$)$_2$ | I—CH(CH$_3$)$_2$ | | |

EXAMPLE 12

Methyl erythro-(E)-7-[1-ethyl-5-(4-fluorophenyl)-1,2-dihydro-7-isopropyl-2-oxo-1,8-naphthyridin-6yl]-3,5-dihydroxy-hept-6-enoate

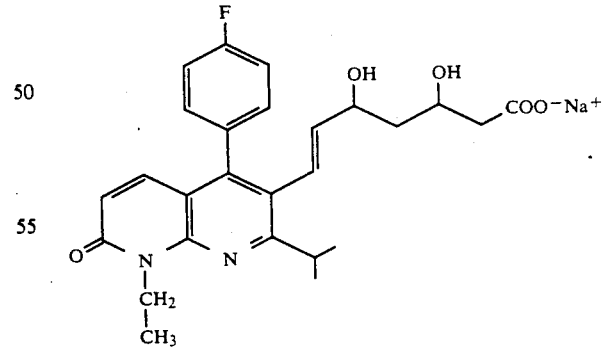

830 mg (2.3 mmol) of the compound from Example 9 are reacted analogously to the procedure of Example 6, 103 mg (3.4 mmol) of sodium hydride, 0.27 ml (2.5 mmol) of ethyl acetate and 2.79 ml (4.6 mmol) of 15% butyl lithium being used.

Yield: 155 mg (14%) colorless crystals, melting point 100° C. (crystallized from ether and petroleum ether).

In analogy to Example 12 are prepared:

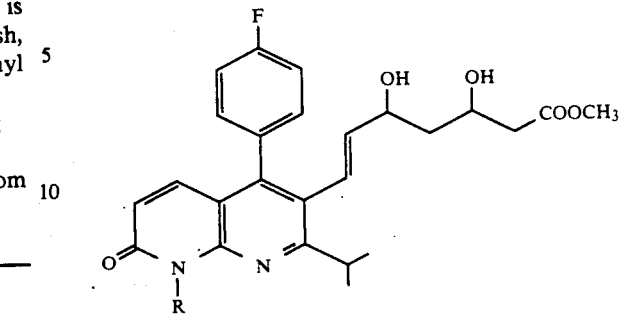

| No. Example | R | Starting compound (Example) | m.p. | $^1$H-NMR (COCl$_3$) |
|---|---|---|---|---|
| 13 | CH$_2$—C$_6$H$_5$ | 10 | | 2,45 (m.2H) 3,4 (m,1H) 3,7 (s,3H) 4,1 (m,1H) 4,35 (n,1H) 5,3 (dd,1H) 5,8 (s,2H) 6,4 (d,1H) 6,6 (d,4H) |
| 14 | —CH(CH$_3$)$_2$ | 11 | | |

EXAMPLE 15

Sodium erythro-(E)-7-[1-ethyl-5-(4-fluorophenyl)-1,2-dihydro-7-isopropyl-2-oxo-1,8-naphthyridin-6-yl]3,5-dihydroxy-hept-6-ene-carboxylate 100 mg (0.2 mmol) of the compound from Example 12 are reacted analogously to the procedure of Example 7.

Yield: 82 mg (81%), colorless foam

FAB-MA: 513 (100%, M+Na+H, 491/20%, M+H)

EXAMPLE 16 trans-6-{2-[5-(4-(Fluorophenyl)-7-isopropyl-2-oxo-1,2-dihydro-1,8-naphthyridin-6-yl]-ethenyl}-4-hydroxy-3,4,5,6-tetrahydro-2H-pyran-2-one

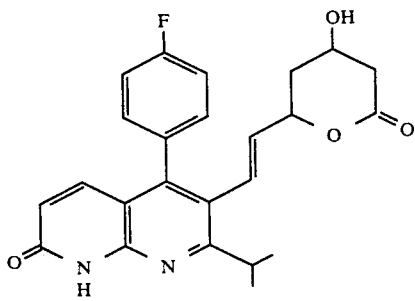

925 mg (2 mmol) of the compound from Example 7 are dissolved in 20 ml of THF and 20 ml of water, the solution is set at pH 5 using 1 N HCl, 384 mg (2 mmol) of N-(3-dimethylaminopropyl)-N,-ethylcarbodiimide are added and the mixture is stirred at room temperature for 1 day. A further 192 g (1 mmol) of the carbodiimide are added and the mixture is stirred for 2 more days. Extraction is carried out with ethyl acetate; drying of the organic phase and chromatography are carried out on 30 g of silica gel (230 to 400 mesh) using chloroform and chloroform/methanol (5:1), and crystallization from chloroform/ether/petroleum ether gives 179 mg (21%) of colorless crystals of m.p.: 233° C.

EXAMPLE 17 trans-6-(2-[1-Benzyl-5-(4-fluorophenyl)-7-isopropyl-2-oxo-1,2-dihydro-1,8-naphthyrihydroxy-6-yl]-ethyl}-4-hydroxy-3,4,5,6-tetrahydro-2H-pyzan-2-one

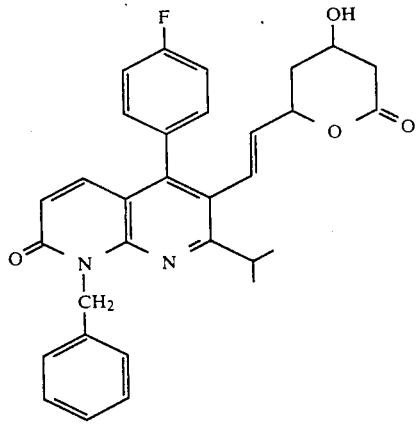

A solution of 73 mg (0.65 mmol) of potassium tert.-butoxide in 1 ml of DMF and a solution of 110 mg (0.65 mmol) of benzyl bromide in 1 ml of DMF are added to a suspension of 250 mg (0.59 mmol) of the compound from Example 16 in 5 ml of DMF and the mixture is stirred at 60° C. for 2.5 h. Working up as in Example 8 gives 115 mg (38%) of colorless foam.

$^1$H-NMR (CDCl$_3$): δ=1.25 (d, 6H); 1.3-1.7 (m, 2H); 2.6 (m, 2H); 3.4 (sept, 1H); 4.2 (m, 1H); 5.1 (m, 1H); 5.3 (dd, 3H); 5.8 (s, 2H); 6.5 (d, 1H); 6.6 (d, 1H); 7.0-7.3 (m, 8H); 7.5 (m, 2H).

EXAMPLE 18 trans-6-({2-[1-cyanomethyl-5-(4-fluorophenyl)-7-isopropyl-oxo-1,2-dihydro-1,8-naphthyridin-6-yl]-ethenyl}-4-hydroxy-3,4,5,6-tetrahydro-2H-pyran-2-one

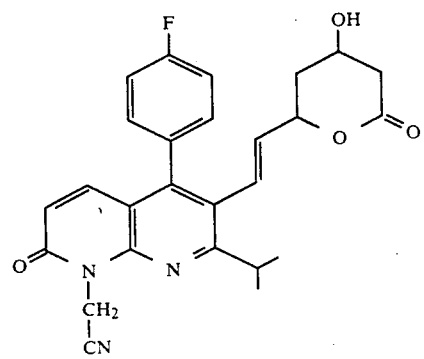

The title compound is prepared analogously to the procedure of Example 8 from 120 mg (0.28 mmol) of the compound from. Example 7, 57 mg (0.5 mmol) of potassium tert.-butoxide and 38 mg (0.5 mmol) of chloroacetonitrile.

Yield: 68 mg (53%) of beige oil.

$^1$H-NMR (CDCl$_3$) δ=1.37 (d, 6H); 1.4-1.8 (m, 2H); 2.25 (b, 1H); 2.65 (m, 2H); 3.45 (sept, 1H); 4.25 (m, 1H); 5.15 (m, 1H); 5.38 (dd, 1H); 5.47 (s, 2H); 6.03 (d, 1H); 6.12 (d, 1H); 7.13 (m, 4H); 7.38 (d, 1H).

EXAMPLE 19

(E)-3-[2-Chloro-5-(4-fluorophenyl)-7-isopropyl-1,8-naphthyridin-6-yl]-prop-2-enal

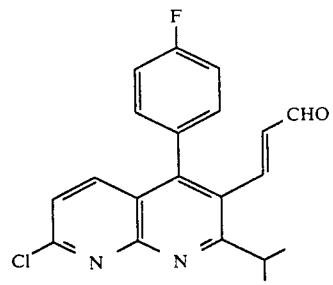

7.8 g (23 mmol) of the compound from Example 5 are heated to 75° C. in 20 ml of phosphorus oxychloride. After a clear solution has formed, the mixture is concentrated in vacuo, the residue is dissolved in ethyl acetate, and the solution is poured into ice water and stirred vigorously. The aqueous phase is extracted twice with ethyl acetate, the combined organic phases are dried and the solvent is stripped off. 5.78 g (71%) of colorless crystals of m.p.: 142° C. crystallize from ether.

The compounds shown in Table 1 are prepared by the following procedure or by analogous methods:

A solution of 167 mg (1.55 mmol) of benzyl alcohol in 1 ml of THF is added dropwise at 0° C. to a suspension of 46 mg (1.55 mmol) of 80% strength sodium hydride in 5 ml of THF and the mixture is stirred for 15 min, A solution of 0.5 g (1.4 mmol) of the compound from Example 19 in 5 ml of THF is added dropwise at the same temperature and the mixture is then stirred at room temperature for 2.5 h. 1.6 ml of acetic acid in 20 ml of water are added, the mixture is extracted twice with 20 ml of ethyl acetate, the combined organic phases are dried and concentrated, and the residue is chromatographed on 20 g of silica gel 230–400 mesh using petroleum ether/ethyl acetate 6:1>3:1.

286 mg (49%) of colorless crystals of m.p.: 182° C. crystallize from ether/petroleum ether.

TABLE 1

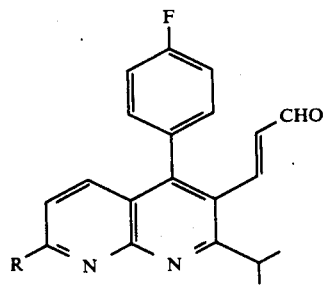

| Example No. | R | Reagent, base, conditions | m.p. (°C.) (solvent) | Yield (%) |
|---|---|---|---|---|
| 20 | —OCH$_2$—C$_6$H$_5$ | HO—CH$_2$—C$_6$H$_5$, NaH, 2.5 h, RT, tetrahydrofuran | 182 ether/petroleum ether | 49 |
| 21 | —OCH$_3$ | NaOCH$_3$, 2 h, RT, tetrahydrofuran | 178 CH$_2$Cl$_2$/petroleum ether | 26 |
| 22 | —O—CH$_2$—C(CH$_3$)$_3$ | HO—CH$_2$—C(CH$_3$)$_3$, NaH, 10 min, reflux, tetrahydrofuran | oil | 26 |
| 23 | S—CH$_2$—C$_6$H$_5$ | HS—CH$_2$—C$_6$H$_5$, DBU 4 h, RT, tetrahydrofuran | 208 | 61 |
| 24 | N—CH$_2$—C$_6$H$_5$ \| CH$_3$ | H—N—CH$_2$—C$_6$H$_5$ \| CH$_3$ 1 h, reflux, dioxane | 158 | 31 |

The compounds shown in Table 2 were prepared from the compounds of Examples 19, 20, 21, 22, 23 and 24 in analogy to the procedure of Example 12.

TABLE 2

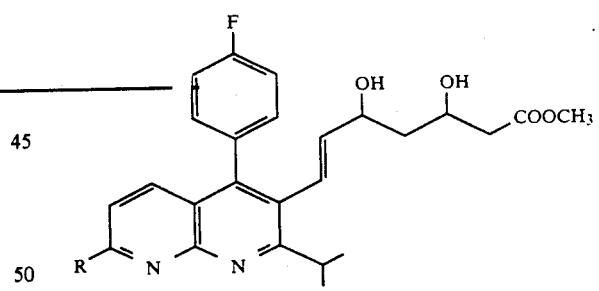

| Example No. | R | m.p. (°C.) solvent | $^1$H-NMR (CDCl$_3$) |
|---|---|---|---|
| 25 | —O—CH$_2$—C$_6$H$_5$ | 170 ether | |
| 26 | —OCH$_3$ | 155 ether/petroleum ether | |
| 27 | —O—CH$_2$—C(CH$_3$)$_3$ | amorphous | 1.08 (s, 9H); 2.45 (m, 2H); 3.73 (s, 3H); 4.1 (m, 1H); 4.3 (s, 2H); 4.36 (m, 1H); 6.57 (d, 1H); 7.15 (m, 4H); 7.58 (d, 1H) |
| 28 | —S—CH$_2$—C$_6$H$_5$ | 165 | |
| 29 | —N—CH$_2$—C$_6$H$_5$ \| CH$_3$ | 134 ether | |
| 30 | Cl | 207 ether | |

The compounds shown in Table 3 were prepared in analogy to the procedure of Example 7.

TABLE 3

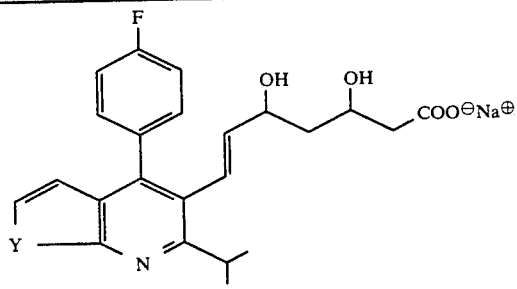

| Example No. | Y | Starting Compound | Yield (%) | m.p. °C. | FAB—MS |
|---|---|---|---|---|---|
| 31 | Cl—C=N— | 30 | 92 | decomposition from 150° | |
| 32 | ⌬—CH₂—O—C=N— | 25 | 100 | amorphous | 575 (M + Na) 553 (M + Na) |
| 33 | 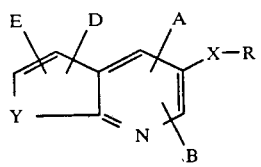 | 10 | 92 | | |

It will be appreciated that the instant specification and claims are set forth by way of illustration and not limitation, and that various modifications and changes may be made without departing from the spirit and scope of the present invention.

What is claimed is:

1. A substituted 1,8-naphthyridine of the formula $$\begin{array}{c} E \diagdown D \diagup A \\ \phantom{E} | \phantom{D} | \phantom{A} X-R \\ Y \diagdown \phantom{|} \diagup \\ \phantom{Y} = N \\ \phantom{Y} B \end{array}$$

in which

A
represents a 3- to 7-membered heterocycle which contains 1 to 4 sulphur, oxygen or nitrogen heteroatoms and which is optionally substituted by identical or different substituents said substituents being halogen, trifluoromethyl, trifluoromethoxy, straight-chain or branched alkyl, alkoxy or alkoxycarbonyl in each case having up to 8 carbon atoms or by aryl having 6 to 10 carbon atoms, or A
represents aryl having 6 to 10 carbon atoms which is optionally substituted by identical or different substituents said substituents being straight-chain or branched alkyl, alkylthio, alkylsulphonyl, alkoxy or alkoxycarbonyl in each case having up to 10 carbon atoms, which may in turn be substituted by hydroxyl, alkoxy having up to 6 carbon atoms, phenyl or by a group of the formula $-NR^1R^2$,
in which
$R^1$ and $R^2$ are identical or different and
denote hydrogen, aryl or arylsulphonyl having 6 to 10 carbon atoms, straight-chain or branched alkyl or alkylsulphonyl having up to 8 carbon atoms, where the last mentioned radicals are optionally substituted by aryl having 6 to 10 carbon atoms,
or $R^1$ and $R^2$ each independently denote a group of the formula $-COR^3$ in which
$R^3$
denotes straight-chain or branched alkyl or alkoxy having up to 8 carbon atoms, or phenyl,
or the A aryl substituent may be aryl, aryloxy, arylthio or arylsulphonyl having 6 to 10 carbon atoms, or halogen, nitro, cyano, trifluoromethyl, trifluoromethoxy, trifluoromethylthio, benzyloxy or a group of the formula $-NR^1R^2$, in which
$R^1$ and $R^2$ have the abovementioned meaning,
represents cycloalkyl having 3 to 8 carbon atoms,
represents straight-chain or branched alkyl having up to 12 carbon atoms, which is optionally substituted by halogen, trifluoromethyl or alkylthio having up to 8 carbon atoms,
or B represents aryl having 6 to 10 carbon atoms, which is optionally substituted by halogen, cyano, nitro, trifluoromethyl, straight-chain or branched alkyl, alkoxy or alkoxycarbonyl in each case having up to 8 carbon atoms, or amino,
D and E are identical or different and
represent hydrogen, halogen, mercapto, hydroxyl, alkoxy having up to 8 carbon atoms, straight-chain or branched alkyl having up to 10 carbon atoms, which is optionally substituted by hydroxyl, phenoxy, halogen, trifluoromethyl or alkylthio having up to 8 carbon atoms, or represents a group of the formula $-NR^1R^2$, in which $R^1$ and $R^2$ have the abovementioned meaning, or D and E each independently represent aryl, aryloxy or arylthio having 6 to 10 carbon atoms, which is optionally substituted by halogen, cyano, nitro, trifluoromethyl, straight-chain or branched alkyl, alkoxy or alkoxycarbonyl in each case having up to 8 carbon atoms, or amino,

Y represents a group of the formula $$-\underset{J}{C}=N- \quad \text{or} \quad -\underset{\underset{Z}{\|}}{C}-\underset{G}{N}-$$

in which

J denotes hydrogen, hydroxyl, mercapto or halogen, or denotes straight-chain or branched alkyl, alkoxy or alkylthio having up to 10 carbon atoms, which are optionally substituted by phenyl, or denotes aryloxy, benzyloxy or arylthio having 6 to 10 carbon atoms or a group of the formula $-NR^1R^2$, in which $R^1$ and $R^2$ have the abovementioned meaning,

Z denotes oxygen or sulphur,

G denotes hydrogen, straight-chain or branched alkyl or alkenyl in each case having up to 10 carbon atoms, which is optionally substituted by halogen, cyano, alkoxy having up to 8 carbon atoms, benzyloxy, aryl or aryloxy having 6 to 10 carbon atoms, by a 5- to 7-membered heterocycle having 1 to 4 nitrogen, oxygen or sulphur heteroatoms or by a group of the formula $-NR^1R^2$, $-COR^3$ or $-COOR^4$, in which $R^1$, $R^2$ and $R^3$ have the abovementioned meaning, $R^4$ denotes hydrogen or straight-chain or branched alkyl having up to 10 carbon atoms, which is optionally substituted by hydroxyl, phenyl, halogen or cyano, or denotes aryl having 6 to 10 carbon atoms, which may in turn be substituted by halogen, amino, hydroxyl, nitro or cyano,

X represents a group of the formula $-CH_2-CH_2-$ or $-CH=CH-$, and

R represents a group of the formula $$-\underset{\underset{OH}{|}}{CH}-CH_2-\underset{\underset{OH}{|}}{\overset{\overset{R^5}{|}}{C}}-CH_2-COOR^6 \quad \text{or} \quad HO\overset{R^5}{\diagdown}\diagup\diagdown\diagup^{O}_{O}$$

in which $R^5$ denotes hydrogen or straight-chain or branched alkyl having up to 10 carbon atoms and $R^6$ denotes hydrogen or straight-chain or branched alkyl having up to 10 carbon atoms, which may be substituted by phenyl, or $R^6$ denotes aryl having 6 to 10 carbon atoms or a physiologically tolerable cation.

2. A substituted 1,8-naphthyridine according to claim 1 of the formula in which

A represents pyridyl or pyrimidyl, which is optionally substituted by identical or different substituents said substituents being fluorine, chlorine, bromine, trifluoromethyl, straight-chain or branched alkyl having up to 6 carbon atoms or phenyl, or A represents phenyl or naphthyl, which is optionally substituted by identical or different substituents said substituents being straight-chain or branched alkyl, alkylthio, alkylsulphonyl, alkoxy or alkoxycarbonyl in each case having up to 8 carbon atoms, which may in turn be substituted by hydroxyl, alkoxy having up to 4 carbon atoms, phenyl or by a group of the formula $-NR^1R^2$, in which $R^1$ and $R^2$ are identical or different and denote hydrogen, phenyl, phenylsulphonyl, straight-chain or branched alkyl or alkylsulphonyl having up to 6 carbon atoms, benzyl or benzylsulphonyl, or denote a group of the formula $-COR^3$, in which $R^3$ denotes straight-chain or branched alkyl or alkoxy having up to 6 carbon atoms or phenyl, or the phenyl or naphthyl may be substituted by phenyl, phenyloxy, fluorine, chlorine, bromine, nitro, cyano, trifluoromethyl, trifluoromethoxy, benzyloxy or by a group of the formula $-NR^1R^2$, in which $R^1$ and $R^2$ have the abovementioned meaning,

B represents cyclopropyl, cyclobutyl, cyclopentyl or cyclohexyl, or represents straight-chain or branched alkyl having up to 10 carbon atoms, which may optionally be substituted by fluorine, chlorine, bromine, trifluoromethyl or methylthio, D and E are identical or different and represent hydrogen, hydroxyl, alkoxy having up to 6 carbon atoms, straight-chain or branched alkyl having up to 8 carbon atoms, phenyl or a group of the formula $-NR^1R^2$, in which $R^1$ and $R^2$ have the abovementioned meaning, Y
represents a group of the formula

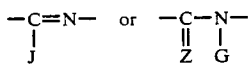

in which

J
denotes hydrogen, hydroxyl, mercapto, fluorine, chlorine or bromine, or denotes straight-chain or branched alkyl, alkoxy or alkylthio having up to 8 carbon atoms, which are optionally substituted by phenyl, or denotes phenoxy, benzyloxy or a group of the formula $-NR^2R^2$, in which $R^1$ and $R^2$ have the abovementioned meaning, Z
oxygen or sulphur, G
denotes hydrogen, straight-chain or branched alkyl or alkenyl in each case having up to 8 carbon atoms, which is optionally substituted by fluorine, chlorine, bromine, cyano, alkoxy having up to 6 carbon atoms, phenyl, phenoxy, benzyloxy, pyrryl, furyl or by a group of the formula $-NR^1R^2$, $-COR^3$ or $-COOR^4$, in which $R^1$, $R^2$ and $R^3$ have the abovementioned meaning, $R^4$
denotes hydrogen, straight-chain or branched alkyl having up to 8 carbon atoms, which is optionally substituted by hydroxyl, phenyl, fluorine, chlorine or bromine, or denotes phenyl which may in turn be substituted by fluorine, chlorine, bromine or hydroxyl, X
represents a group of the formula $-CH_2-CH_2-$ or $-CH=CH-$ and R
represents a group of the formula

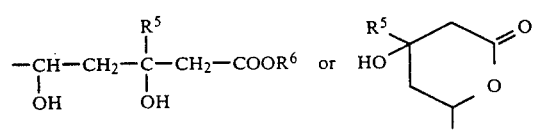

in which $R^5$
denotes hydrogen or straight-chain or branched alkyl having up to 8 carbon atoms and $R^6$
denotes hydrogen or straight-chain or branched alkyl having up to 8 carbon atoms, or benzyl or denotes phenyl or a physiologically tolerable cation.

3. A substituted 1,8-naphthyridine according to claim 1, in which

A
represents phenyl which is optionally substituted by identical or different substituents said substituents being straight-chain or branched alkyl having up to 6 carbon atoms, which may in turn be substituted by hydroxyl, methoxy, ethoxy, propoxy or phenyl, or is substituted by phenyl, phenoxy, fluorine, chlorine, bromine or benzyloxy, B
represents cyclopropyl, cyclobutyl, cyclopentyl or cyclohexyl, or represents methyl, ethyl, propyl, isopropyl, butyl, isobutyl, tert.butyl or trifluoromethyl, D and E are identical or different and represent hydrogen, hydroxyl, methyl, ethyl, propyl, isopropyl, methoxy or ethoxy, Y
represents a group of the formula

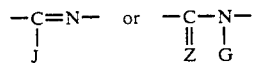

in which

J
denotes hydrogen, hydroxyl, fluorine or chlorine, or denotes straight-chain or branched alkyl, alkoxy or alkylthio having up to 6 carbon atoms, which are optionally substituted by phenyl, or denotes benzyloxy or a group of the formula $-NR^1R^2$, in which $R^1$ and $R^2$ are identical or different and denote hydrogen or straight-chain or branched alkyl having up to 4 carbon atoms, or benzyl, Z
denotes oxygen or sulphur, G
denotes hydrogen, straight-chain or branched alkyl having up to 6 carbon atoms, which is optionally substituted by fluorine, chlorine, cyano, alkoxy having up to 4 carbon atoms, phenyl, benzyloxy or by a group of the formula $-COR^3$ or $-COOR^4$, in which $R^3$
denotes straight-chain or branched alkyl or phenyl, $R^4$
denotes hydrogen, straight-chain or branched alkyl having up to 6 carbon atoms or phenyl, X
represents a group $-CH=CH-$ or $-CH_2-CH_2-$ and R
represents a group of the formula

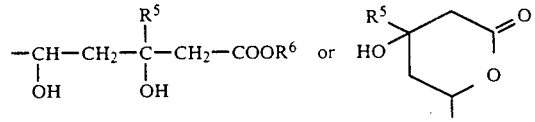

in which $R^5$
denotes hydrogen, methyl, ethyl, propyl, isopropyl, butyl, isobutyl or tert.butyl and $R^6$
denotes hydrogen, methyl, ethyl, propyl, isopropyl, butyl, isobutyl, tert.butyl or benzyl, or denotes a sodium, potassium, calcium, magnesium or ammonium ion.

4. A substituted 1,8-naphthyridine according to claim 1, in the form of a racemate or as an individual stereoisomer or enantiomer.

5. A pharmaceutical composition useful as an inhibitor of 3-hydroxy-3-methyl-glutaryl-coenzyme A reductase comprising at least one substituted 1,8-naphthyridine according to claim 1 and an inert, non-toxic pharmaceutically suitable excipient or solvent.

6. A pharmaceutical composition useful for the treatment of hyperlipoproteinaemia or atherosclerosis or for lowering blood cholesterol content comprising at least one substituted 1,8-naphthyridine according to claim 1 and an inert, non-toxic pharmaceutically suitable excipient or solvent.

7. A method of inhibiting 3-hydroxy-3-methyl-glutaryl-coenzyme A reductase activity comprising administering to a patient in need of such an inhibiting treatment an effective amount of at least one substituted 1,8-naphthyridine according to claim 1.

8. A method of teating hyperlipoproteinaemia or atherosclerosis comprising administering to a patient in need of such treatment an effective amount of at least one substituted 1,8-naphthyridine according to claim 1.

9. A method of lowering blood cholesterol content in a patient comprising administering to a patient requiring lowering of blood cholesterol content an effective amount of at least one substituted 1,8-naphthyridine according to claim 1.

* * * * *

UNITED STATES PATENT AND TRADEMARK OFFICE
CERTIFICATE OF CORRECTION

PATENT NO. : 5,034,399

DATED : July 23, 1991

INVENTOR(S) : Hubsch et al.

It is certified that error appears in the above-identified patent and that said Letters Patent is hereby corrected as shown below:

Title page, item [56] FOREIGN PATENT DOCUMENTS: Delete " 02322350 " and substitute -- 2322350 --

Title page, item [57] ABSTRACT: Line 26 delete " $-CH_2CH_2-$ " and substitute -- $-CH_2-CH_2-$ --

Col. 36, line 55  Before " represents " insert -- B --

Col. 39, line 21  Delete " $-NR^2R^2$ " and substitute -- $-NR^1R^2$ --

Signed and Sealed this

Twenty-second Day of February, 1994

Attest:

BRUCE LEHMAN

*Attesting Officer*   *Commissioner of Patents and Trademarks*